United States Patent
Riebel et al.

(10) Patent No.: US 6,602,827 B1
(45) Date of Patent: *Aug. 5, 2003

(54) HERBICIDAL 5-CHLORODIFLUOROMETHYL-1,3,4-THIADIAZOL-2-YL-OXYACETANILIDES

(75) Inventors: Hans-Jochem Riebel, Selters (DE); Heinz Förster, Kadenbach (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/048,088
(22) PCT Filed: Jul. 18, 2000
(86) PCT No.: PCT/EP00/06851
§ 371 (c)(1), (2), (4) Date: Jan. 24, 2002
(87) PCT Pub. No.: WO01/09109
PCT Pub. Date: Feb. 8, 2001

(30) Foreign Application Priority Data

Jul. 30, 1999 (DE) .......................... 199 35 964

(51) Int. Cl.[7] .............................. A01N 43/82
(52) U.S. Cl. ........................ 504/263; 548/136
(58) Field of Search ................... 548/136; 504/263

(56) References Cited

U.S. PATENT DOCUMENTS

| | | | |
|---|---|---|---|
| 4,910,316 A | 3/1990 | Diehr et al. | 548/202 |
| 4,968,342 A | 11/1990 | Förster et al. | 71/90 |
| 4,988,380 A | * 1/1991 | Forster et al. | 71/90 |
| 5,101,034 A | 3/1992 | Schmidt et al. | 548/136 |
| 5,147,443 A | 9/1992 | Diehr et al. | 71/67 |
| 5,177,090 A | 1/1993 | Diehr et al. | 514/363 |

FOREIGN PATENT DOCUMENTS

| | | | |
|---|---|---|---|
| DE | 19933936 | * | 1/2001 |
| EP | 148 501 | | 7/1985 |
| EP | 0 348 735 | | 1/1990 |
| EP | 348 737 | | 1/1990 |
| EP | 626 380 | | 11/1994 |

OTHER PUBLICATIONS

Klaus–Helmut Muller et al, "Preparation of heteroaryloxacetanilides as herbicides"; CA: 134:115961.*

* cited by examiner

Primary Examiner—Joseph K. McKane
Assistant Examiner—Robert Shiao
(74) Attorney, Agent, or Firm—Richard E. L. Henderson; John E. Mrozinski, Jr.

(57) ABSTRACT

The invention relates to novel 5-chlorodifluoromethyl-1,3,4-thiadiazol-2-yl-oxyacetanilides of the general formula (I)

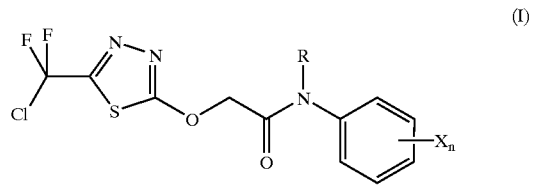

in which
n represents the number 0, 1, 2 or 3,
R represents straight-chain or branched alkyl having 1 to 4 carbon atoms, and
X represents nitro, cyano, halogen or represents in each case optionally cyano-, halogen- or $C_1$–$C_4$-alkoxy-substituted alkyl, alkoxy, alkylthio, alkylsulphinyl or alkylsulphonyl having in each case 1 to 4 carbon atoms, except for the compounds N-methyl-5-chlorodifluoromethyl-1,3,4-thiadiazol-2-yl-oxyacetanilide, N-ethyl-5-chlorodifluoromethyl-1,3,4-thiadiazol-2-yl-oxyacetanilide, 4-chloro-N-methyl-(5-chlorodifluoromethyl-1,3,4-thiadiazol-2-yl)-oxyacetanilide and 3-trifluoromethyl-N-methyl-(5-chlorodifluoromethyl-1,3,4-thiadiazol-2-yl)-oxyacetanilide, N-i-propyl-5-chlorodifluoromethyl-1,3,4-thiadiazol-2-yl-oxyacetanilide, and 4-fluoro-N-methyl-(5-chlorodifluoromethyl-1,3,4-thiadiazol-2-yl)-oxyacetanilide and 4-fluoro-N-ethyl-(5-chlorodifluoromethyl-1,3,4-thiadiazol-2-yl)-oxyacetanilide,
and to a process for their preparation and to their use as herbicides.

8 Claims, No Drawings

HERBICIDAL 5-CHLORODIFLUOROMETHYL-1,3,4-THIADIAZOL-2-YL-OXYACETANILIDES

FIELD OF THE INVENTION

The invention relates to novel 5-chlorodifluoromethyl-1,3,4-thiadiazol-2-yl-oxyacetanilides, to a process for their preparation and to their use as herbicides.

BACKGROUND OF THE INVENTION

It is already known that certain 5-chlorodifluoromethyl-1,3,4-thiadiazol-2-yl-oxyacetanilides such as, for example, the compounds N-methyl-5-chlorodifluoromethyl-1,3,4-thiadiazol-2-yl-oxyacetanilide, N-ethyl-5-chlorodifluoromethyl-1,3,4-thiadiazol-2-yl-oxyacetanilide, 4-chloro-N-methyl-(5-chlorodifluoromethyl-1,3,4-thiadiazol-2-yl)-oxyacetanilide and 3-trifluoromethyl-N-methyl-(5-chlorodifluoromethyl-1,3,4-thiadiazol-2-yl)-oxyacetanilide (cf.EP-A-148501/ U.S. Pat. No. 4,798,731), the compound N-i-propyl-5-chlorodifluoromethyl-1,3,4-thiadiazol-2-yl-oxyacetanilide (cf. EP-A-348737/U.S. Pat. No. 4,968,342) and the compounds 4-fluoro-N-methyl-(5-chlorodifluoromethyl-1,3,4-thiadiazol-2-yl)-oxyacetanilide and 4-fluoro-N-ethyl-(5-chlorodifluoromethyl-1,3,4-thiadiazol-2-yl)-oxyacetanilide have herbicidal properties (cf. EP-A-626380). However, the activity of these prior-art compounds is, in particular at low application rates and concentrations, not entirely satisfactory in all areas of use.

SUMMARY OF THE INVENTION

The present invention provides a 5-chlorodifluoromethyl-1,3,4-thiadiazol-2-yl-oxyacetanilide of the general formula (I)

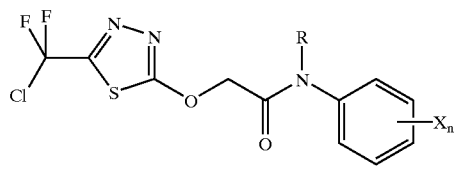

wherein n represents the number 0, 1, 2 or 3,

R represents straight-chain or branched alkyl having 1 to 4 carbon atoms, and

X represents nitro, cyano, halogen or represents in each case optionally cyano-, halogen- or $C_1$–$C_4$-alkoxy-substituted alkyl, alkoxy, alkylthio, alkylsulphinyl or alkylsulphonyl having in each case 1 to 4 carbon atoms, except for the compounds N-methyl-5-chlorodifluoromethyl-1,3,4-thiadiazol-2-yl-oxyacetanilide, N-ethyl-5-chlorodifluoromethyl-1,3,4-thiadiazol-2-yl-oxyacetanilide, 4-chloro-N-methyl-(5-chlorodifluoromethyl-1,3,4-thiadiazol-2-yl)-oxyacetanilide and 3-trifluoromethyl-N-methyl-(5-chlorodifluoromethyl-1,3,4-thiadiazol-2-yl)-oxyacetanilide, N-i-propyl-5-chlorodifluoromethyl-1,3,4-thiadiazol-2-yl-oxyacetanilide, and 4-fluoro-N-methyl-(5-chlorodifluoromethyl-1,3,4-thiadiazol-2-yl)-oxyacetanilide and 4-fluoro-N-ethyl-(5-chlorodifluoromethyl-1,3,4-thiadiazol-2-yl)-oxyacetanilide, The present invention also provides a process for preparation of the compound. The compound has herbicidal activity.

This invention, accordingly, provides novel 5-chlorodifluoromethyl-1,3,4-thiadiazol-2-yl-oxyacetanilides of the general formula (I)

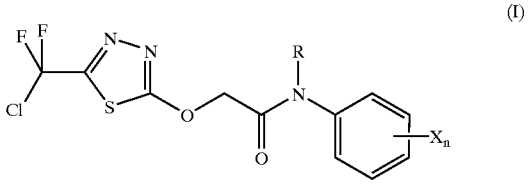

in which n represents the number 0, 1, 2 or 3,

R represents straight-chain or branched alkyl having 1 to 4 carbon atoms, and

X represents nitro, cyano, halogen or represents in each case optionally cyano-, halogen- or $C_1$–$C_4$-alkoxy-substituted alkyl, alkoxy, alkylthio, alkylsulphinyl or alkylsulphonyl having in each case 1 to 4 carbon atoms, except for the compounds N-methyl-5-chlorodifluoromethyl-1,3,4-thiadiazol-2-yl-oxyacetanilide, N-ethyl-5-chlorodifluoromethyl-1,3,4-thiadiazol-2-yl-oxyacetanilide, 4-chloro-N-methyl-(5-chlorodifluoromethyl-1,3,4-thiadiazol-2-yl)-oxyacetanilide and 3-trifluoromethyl-N-methyl-(5-chlorodifluoromethyl-1,3,4-thiadiazol-2-yl)-oxyacetanilide (cf. EP-A-149501/U.S. Pat. No. 4,798,731), N-i-propyl-5-chlorodifluoromethyl-1,3,4-thiadiazol-2-yl-oxyacetanilide (cf. EP-A-348737/ U.S. Pat. No. 4,968,342), and 4-fluoro-N-methyl-(5-chlorodifluoromethyl-1,3,4-thiadiazol-2-yl)-oxyacetanilide and 4-fluoro-N-ethyl-(5-chlorodifluoromethyl-1,3,4-thiadiazol-2-yl)-oxyacetanilide (cf. EP-A-626380)-.

Preferred substituents or ranges of the radicals present in the formulae listed above and below are described below.

n preferably represents the number 0, 1 or 2.

R preferably represents methyl, ethyl, n- or i-propyl, n-, i-, s- or t-butyl.

X preferably represents nitro, cyano, fluorine, chlorine, bromine or represents in each case optionally cyano-, fluorine-, chlorine-, methoxy- or ethoxy-substituted methyl, ethyl, n- or i-propyl, methoxy, ethoxy, methylthio, ethylthio, methylsulphinyl, ethylsulphinyl, methylsulphonyl or ethylsulphonyl.

n particularly preferably represents the number 0, 1 or 2.

R particularly preferably represents methyl, ethyl, n- or i-propyl, s- or t-butyl.

X particularly preferably represents nitro, cyano, fluorine, chlorine, bromine or represents in each case optionally fluorine- or chlorine-substituted methyl, ethyl, methoxy, ethoxy, methylthio, ethylthio, methylsulphinyl, ethylsulphinyl, methylsulphonyl or ethylsulphonyl.

n very particularly preferably represents the number 0, 1 or 2.

R very particularly preferably represents methyl, ethyl, n- or i-propyl, s- or t-butyl.

X very particularly preferably represents cyano, fluorine, chlorine, bromine, methyl, ethyl, trifluoromethyl, methoxy or trifluoromethoxy.

The general or preferred radical definitions listed above apply both to the end products of the formula (I) and, correspondingly, to the starting materials or intermediates required in each case for the preparation. These radical definitions can be combined with one another if desired, i.e. including combinations between the given preferred ranges.

Preference according to the invention is given to those compounds of the formula (I) which contain a combination of the meanings listed above as being preferred.

Particular preference according to the invention is given to those compounds of the formula (I) which contain a combination of the meanings listed above as being particularly preferred.

Very particular preference according to the invention is given to those compounds of the formula (I) which contain a combination of the meanings listed above as being very particularly preferred.

Optionally substituted radicals can be mono- or polysubstituted, where, in the case of polysubstitution, the substituents can be identical or different.

Examples of the compounds of the general formula (I) according to the invention are listed in the groups below.

Group 1

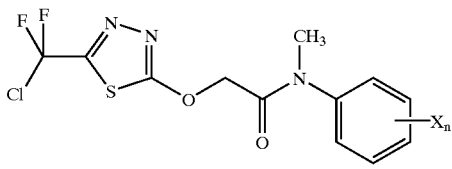

Examples of the meanings of $X_n$ and (as a prefix in brackets) the positions of $X_n$ are given below:

n=0 (i.e. X=H);
n=1 (i.e. X different from H); in this case, X represents, for example, (2) CN, (3) CN, (4) CN, (2) F, (3) F, (4) F, (2) Cl, (3) Cl, (4) Cl, (2) CH$_3$, (3) CH$_3$, (4) CH$_3$, (2) C$_2$H$_5$, (3) C$_2$H$_5$, (4) C$_2$H$_5$, (2) CF$_3$, (3) CF$_3$, (4) CF$_3$, (2) Br, (3), Br, (4) Br, (2) OCH$_3$, (3) OCH$_3$, (4) OCH$_3$, (2) OCF$_3$, (3) OCF$_3$, (4) OCF$_3$;
n=2 (i.e. X different from H); X is then located in two positions (with identical or different meaning) and represents, for example, (2,3) F$_2$, (2,4) F$_2$, (2,5) F$_2$, (3,4) F$_2$, (3,5) F$_2$, (2) F/(3) Cl, (2) F/(4) Cl, (2) F/(5) Cl, (3) F/(4) Cl, (2) F/(3) Br, (2) F/ (4) Br, (2) F/(5) Br, (2) F/(3) CH$_3$, (2) F/(4) CH$_3$, (2) F/(5) CH$_3$, (3) F/(4) CH$_3$, (2) F/(3) C$_2$H$_5$, (2) F/(4) C$_2$H$_5$, (2) F/(5) C$_2$H$_5$, (2) F/(3) CF$_3$, (2) F/(4) CF$_3$, (2) F/(5) CF$_3$, (2,3) Cl$_2$, (2,4) Cl$_2$, (2,5) Cl$_2$, (3,4) Cl$_2$, (2) Cl/(3) F, (2) Cl/(4) F, (2) Cl/(5) F, (3) Cl/(4) F, (2) Cl/(3) Br, (2) Cl/(4) Br, (2) Cl/(5) Br, (2) Cl/(3) CH$_3$, (2) Cl/(4) CH$_3$, (2) Cl/(5) CH$_3$, (2) Cl/(3) C$_2$H$_5$, (2) Cl/(4) C$_2$H$_5$, (2) Cl/(5) C$_2$H$_5$, (2) Cl/(3) CF$_3$, (2) Cl/(4) CF$_3$, (2) Cl/(5) CF$_3$, (3) Cl/(4) CF$_3$, (2) Br/(3) F, (2) Br/(4) F, (2) Br/(5) F, (2) Br/(3) Cl, (2) Br/(4) Cl, (2Br/(5) Cl, (2), (2) Br/(3) CH$_3$, (2) Br/(4) CH$_3$, (2) Br/(5) CH$_3$, (2) Br/(3) CF$_3$, (2) Br/(4) CF$_3$, (2) Br/(5) CF$_3$, (2,3) (CH$_3$)$_2$, (2,4) (CH$_3$)$_2$, (2,5) (CH$_3$)$_2$, (3,4) (CH$_3$)$_2$, (2) CH$_3$/(3) F, (2) CH$_3$/(4) F, (2) CH$_3$/(5) F, (3) CH$_3$/(4) F, (2) CH$_3$/(3) Cl, (2CH$_3$/(4) Cl, (2) CH$_3$/(5) Cl, (2) CH$_3$/(3) Br, (2) CH$_3$/(4) Br, (2) CH$_3$/(5) Br, (2) CH$_3$/(3) CF$_3$, (2) CH$_3$/(4) CF$_3$, (2) CH$_3$/(5) CF$_3$, (2) C$_2$H$_5$/(3) F, (2) C$_2$H$_5$/(4) F, (2) C$_2$H$_5$/(5) F, (2,3) (CF$_3$)$_2$, (2,4) (CF$_3$)$_2$, (2,5) (CF$_3$)$_2$, (2) CF$_3$/(3) F, (2) CF$_3$/(4) F, (2) CF$_3$/(5) F, (2) CF$_3$/(3) Cl, (2) CF$_3$/(4) Cl, (2) CF$_3$/(5) Cl, (2) Cl/(4) OCH$_3$, (2) Cl/(5) OCH$_3$, (2) F/(4) OCH$_3$, (2) OCF$_3$/(4) F, (2) OCF$_3$/(4) Cl, (2) F/(4) OCF$_3$, (2) Cl/(4) OCF$_3$ Group 2

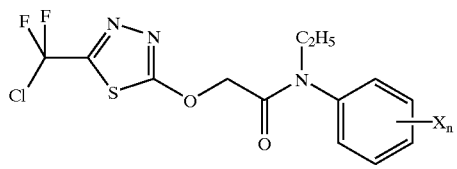

$X_n$ has here the meaning given above in group 1.

Group 3

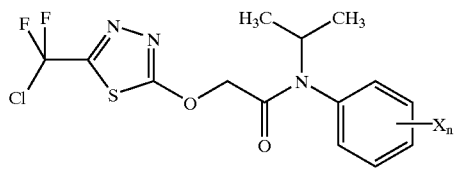

$X_n$ has here the meaning given above in group 1.

Group 4

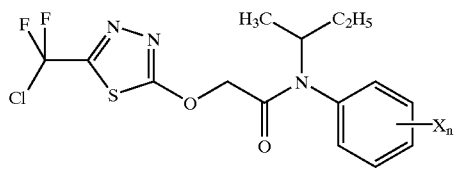

$X_n$ has here the meaning given above in group 1.

Group 5

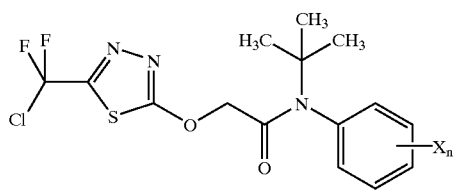

$X_n$ has here the meaning given above in group 1.

The novel 5-chlorodifluoromethyl-1,3,4-thiadiazol-2-yl-oxyacetanilides of the general formula (I) have interesting biological properties. In particular, they have strong and selective herbicidal activity.

The novel 5-chlorodifluoromethyl-1,3,4-thiadiazol-2-yl-oxyacetanilides of the general formula (I) are obtained when 5-chlorodifluoromethyl-2-methylsulphonyl-1,3,4-thiadiazoles of the formula (II)

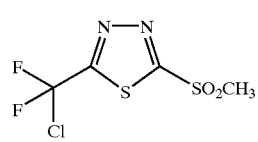

(II)

are reacted with hydroxyacetanilides of the general formula (III)

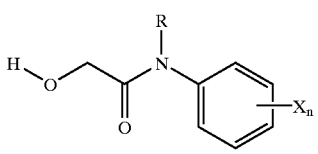

(III)

in which
n, R and X are each as defined above,
if appropriate in the presence of an acid binder and if appropriate in the presence of a diluent.

Using, for example, 5-chlorodifluoromethyl-2-methylsulphonyl-1,3,4-thiadiazole and N-(t-butyl)-N-(3-fluoro-phenyl)-2-hydroxyacetamide as starting materials, the course of the reaction in the process according to the invention can be illustrated by the following formula scheme:

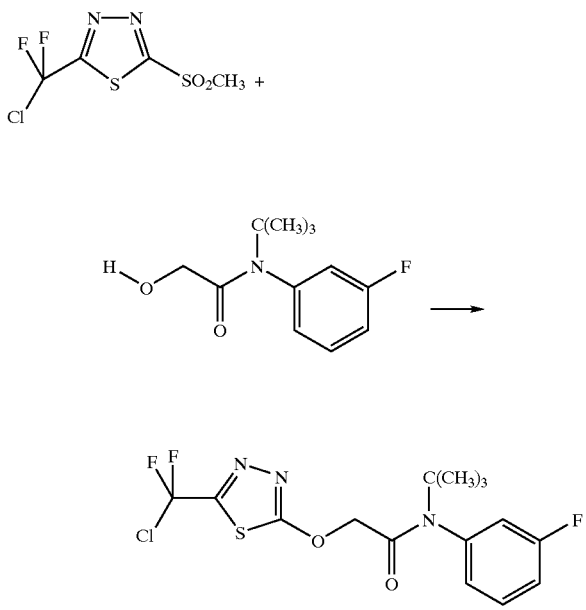

The compound 5-chlorodifluoromethyl-2-methylsulphonyl-1,3,4-thiadiazole of the formula (II) to be used as starting material in the process according to the invention for preparing compounds of the general formula (I) is already known (cf. EP-A-298338).

The compound 5-chlorodifluoromethyl-2-methylsulphonyl-1,3,4-thiadiazole of the formula (II) is obtained when, for example, in a first step, chlorodifluoroacetic acid ($ClF_2C$—COOH) is reacted with methyl dithiocarbazide ($NH_2NH$—C(S)—S—$CH_3$) in the presence of phosphoryl chloride P(O)$Cl_3$ at temperatures between 0° C. and 100° C., and the resulting compound 5-chlorodifluoromethyl-2-methylthio-1,3,4-thiadiazole is reacted with an oxidizing agent, such as, for example, hydrogen peroxide ($H_2O_2$), if appropriate in the presence of a catalyst, such as, for example, sodium tungstate, and if appropriate in the presence of a diluent, such as, for example, acetic acid, at temperatures between 0° C. and 50° C. (cf. the Preparation Examples).

The formula (III) provides a general definition of the hydroxyacetanilides to be used as starting materials in the process according to the invention for preparing compounds of the general formula (I). In the general formula (III), n, R and X each preferably or in particular have those meanings which have already been mentioned above, in connection with the description of the compounds of the general formula (I) according to the invention, as being preferred or as being particularly preferred for n, R and X.

The starting materials of the general formula (III) are known and/or can be prepared by processes known per se (cf. EP-A-18749, EP-A-148501, EP-A-165537, EP-A-308740, EP-A-348735, EP-A-348737, EP-A-626380).

Suitable diluents for carrying out the process according to the invention for preparing the compounds of the general formula (I) are, in addition to water, especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitrites, such as acetonitrile, propionitrile or butyronitrile; amides, such as N,N-dimethylformamide, N,N-dimethylacetamide, N-methyl-formanilide, N-methyl-pyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethylether, diethylene glycol monomethyl ether, diethylene glycol monoethyl ether, mixtures thereof with water or pure water.

Suitable acid binders for the process according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine 4-dimethylamino-pyridine, N-methyl-piperidine, 1,4-diazabicyclo[2.2.2]-octane (DABCO), 1,5-diazabicyclo[4.3.0]-non-5-ene (DBN) or 1,8-diazabicyclo[5.4.0]-undec-7-ene (DBU).

When carrying out the process according to the invention, the reaction temperatures can be varied within a relatively wide range. In general, the process is carried out at temperatures between −20° C. and 100° C., preferably between 0° C. and 60° C.

The process according to the invention is generally carried out under atmospheric pressure. However, it is also possible to carry out the process according to the invention under elevated or reduced pressure—in general between 0.1 bar and 10 bar.

For carrying out the process according to the invention, the starting materials are generally employed in approximately equimolar amounts. However, it is also possible to use a relatively large excess of one of the components. The reaction is generally carried out in a suitable diluent in the presence of an acid binder, and the reaction mixture is generally stirred at the required temperature for several hours. Workup is carried out by customary methods (cf. the Preparation Examples).

The active compounds according to the invention can be used as defoliants, desiccants, haulm killers and, especially, as weedkillers. By weeds in the broadest sense there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledonous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas, Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

According to the invention, it is possible to treat all plants and parts of plants. By plants are to be understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating atomizing, broadcasting, brushing-on and, in the case of propagation material, in particular in the case of seeds, furthermore by one- or multi-layer coating.

Depending on the concentration, the active compounds are suitable for total weed control, for example on industrial terrain and rail tracks and on paths and areas with or without tree growth. Equally, the active compounds according to the invention can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hop fields, on lawns and turf and pastures and for selective weed control in annual crops.

The compounds of the formula (I) according to the invention have strong herbicidal activity and a broad activity spectrum when applied on the soil and on above-ground parts of plants. To a certain extent, they are also suitable for the selective control of monocotyledenous and dicotyledenous weeds in monocotyledenous and dicotyledenous crops, both by the pre-emergence and the post-emergence method.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethylformamide and dimethyl sulphoxide, and water.

Suitable solid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils.

It is possible to use dyestuffs, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Possible components for the mixtures are known herbicides, for example acetochlor, acifluorfen(-sodium), aclonifen, alachlor, alloxydim(-sodium), ametryne, arnidochlor, amidosulfuron, anilofos, asulam, atrazine, azafenidin, azimsulfuron, benazolin(-ethyl), benfuresate, bensulfuron(-methyl), bentazone, benzobicyclon, benzofenap, benzoylprop(-ethyl), bialaphos, bifenox, bispyribac(-sodium), bromobutide, bromofenoxim, bromoxynil, butachlor, butroxydim, butylate, cafenstrole, caloxydim, carbetamide, carfentrazone(-ethyl), chlomethoxyfen, chloramben, chloridazon, chlorimuron(-ethyl), chlomitrofen, chlorsulfuron, chlorotoluron, cinidon(-ethyl), cimnethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epoprodan, EPTC, esprocarb, ethalfluralin, etharnetsulfuron(-methyl), ethofumesate, ethoxyfen, ethoxysulfuron, etobenzanid, fenoxaprop-(-P-ethyl), fentrazamide, flarnprop(-isopropyl), flamprop(-isopropyl-L), flamprop(-methyl), flazasulfuron, florasulam, fluazifop(-P-butyl), fluazolate, flucarbazone, flufenacet, flumetsularn, flumiclorac(-pentyl), flumioxazin, flumipropyn, flumetsulam, fluometuron, fluorochloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiarnide, fomesafen, glufosinate(-ammonium), glyphosate(-isopropylammonium), halosafen, haloxyfop(-ethoxyethyl), haloxyfop(-P-methyl), hexazinone, imazamethabenz-(-methyl), imazamethapyr, imazamox, inazapic, imazapyr, imazaquin, imazethapyr, imazosulfuron, iodosulfuiron(-methyl, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, piperophos, pretilachlor, primisulfuron(-methyl), prometryn, propachlor, propanil, propaquizafop, propisochlor, propyzamide, prosulfocarb, prosulfuiron, pyraflufen(-ethyl), pyrazolate, pyrazosulfuron(-ethyl), pyrazoxyfen, pyribenzoxim, pyributicarb, pyridate, pyriminobac-(-methyl), pyrithiobac(-sodium), quinchlorac, quinmerac, quinoclamine, quizalofop(-P-ethyl), quizalofop(-P-tefuiryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfiron.

A mixture with other known active compounds, such as fumgicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing, scattering.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

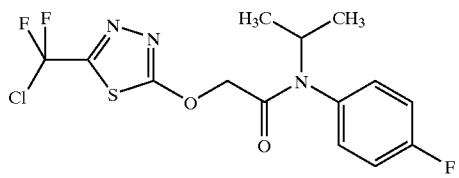

A mixture of 10 g (47 mmol) of N-i-propyl-N-(4-fluorophenyl)-2-hydroxy-acetamide, 11.8 g (47 mmol) of 5-chlorodifluoromethyl-2-methylsulphonyl-1,3,4-thiadiazole and 50 ml of acetone is cooled to −20° C. and, at this temperature, admixed dropwise with stirring with a solution of 3 g (75 mmol) of sodium hydroxide in 8 ml of water. The reaction mixture is stirred at −10° C. for 25 hours and then diluted with water to about three times its original volume and extracted with methylene chloride. The organic phase is washed with water, dried with sodium sulphate and filtered. The filtrate is concentrated under water-pump vacuum, the residue is digested with ligroine and the resulting crystalline product is isolated by filtration with suction.

This gives 10 g (56% of theory) of N-i-propyl-N-(4-fluoro-phenyl)-2-(5-chlorodifluoromethyl-1,3,4-thiadiazol-2-yl-oxy)-acetamide of melting point 98° C.

Analogously to Example 1, and in accordance with the general description of the preparation process according to the invention, it is also possible to prepare, for example, the compounds of the general formula (I) listed in Table 1 below.

TABLE 1

Examples of compounds of the formula (I)

(I)

| Ex. No. | R | (Position) $X_n$ | Physical data |
|---|---|---|---|
| 2 | i-$C_3H_7$ | (4) Cl | m.p.: 78° C. |
| 3 | i-$C_3H_7$ | (3) Cl | m.p.: 71° C. |
| 4 | i-$C_3H_7$ | (3) $CH_3$ | m.p.: 57° C. |
| 5 | i-$C_3H_7$ | (4) $CH_3$ | m.p.: 78° C. |
| 6 | i-$C_3H_7$ | (3) $OCH_3$ | m.p.: 79° C. |
| 7 | i-$C_3H_7$ | (3) F | m.p.: 60° C. |
| 8 | i-$C_3H_7$ | (2,4) $F_2$ | m.p.: 84° C. |

STARTING MATERIAL OF THE FORMULA (II)

Example II-1

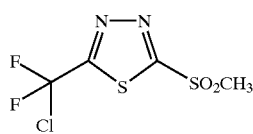

Step 1

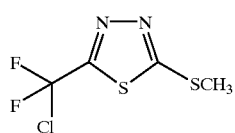

393 g (3 mol) of chlorodifluoroacetic acid are mixed with 372 g (3 mol) of methyl dithiocarbazide. Over a period of two hours, 1000 g (6.54 mol) of phosphoryl chloride are then added dropwise to this mixture, whereupon evolution of gas sets in. The reaction mixture is then heated slowly to from 70° C. to 80° C. and kept at this temperature for about 3 hours, during which evolution of gas slowly ceases. The mixture is then poured onto about 3 kg of ice and allowed to stand until most of the excess phosphoryl chloride has been decomposed. The mixture is then shaken with chloroform and the organic phase is separated off, dried with sodium sulphate and filtered. The filtrate is concentrated under waterpump vacuum and the residue is worked up by distillation under reduced pressure.

This gives 564 g (87% of theory) of 5-chlorodifluoromethyl-2-methylthio-1,3,4-thiadiazole of boiling point 62° C. (at 0.2 mbar).

Step 1

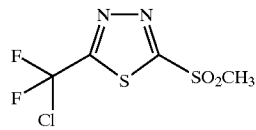

Over a period of two hours, 49.5 g of a 35% strength aqueous hydrogen peroxide solution (0.57 mol of $H_2O_2$) are added dropwise with stirring to a mixture of 22 g (0.10 mol) of 5-chlorodifluoromethyl-2-methylthio-1,3,4-thiadiazole, 1 g of sodium tungstate and 70 ml of acetic acid, the reaction temperature being maintained at from 20° C. to 25° C. At this temperature, the reaction mixture is stirred for 20 hours and then stirred with 150 ml of chloroform. The organic phase is separated off, washed with water, dried with sodium sulphate and filtered. From the filtrate, the solvent is carefully distilled off under reduced pressure.

This gives 22.5 g (91% of theory) of 5-chlorodifluoromethyl-2-methylsulphonyl-1,3,4-thiadiazole of melting point 46° C.

USE EXAMPLES

Example A

Pre-emergence Test

Solvent: 5 parts by weight of acetone
Emulsifier: 1 part by weight of alkylaryl polyglycol ether
To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The active compound concentration in the spray liquor is chosen so that the particular amount of active compound desired is applied in 1000 liters of water per hectare.

After three weeks, the degree of damage to the plants is rated in % damage in comparison to the development of the untreated control. The figures denote:

0%=no effect (like untreated control)
100%=total destruction

In this test, for example, the compound of Preparation Example 1 shows very strong activity against weeds, and it is tolerated well by crop plants, such as, for example, soya and wheat.

TABLE A

Pre-emergence test/greenhouse

| Active compound of Preparation Example No. | Application rate (g of ai./ha) | Wheat | Soya | Eriochloa | Lolium | Setaria | Galium | Matricaria |
|---|---|---|---|---|---|---|---|---|
| 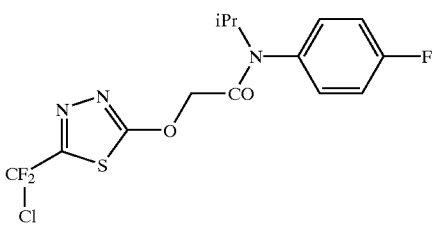 (1) | 125 | 0 | 0 | 100 | 90 | 100 | 90 | 100 |

Example B
Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5 to 15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control.

The figures denote:

0%=no effect (like untreated control))

100%=total destruction

In this test, for example, the compound of Preparation Example 1 shows strong activity against weeds and is tolerated well by crop plants, such as, for example, maize.

What is claimed is:

1. A compound of the formula (I)

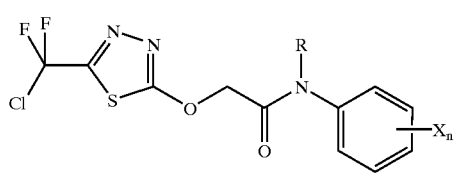

wherein n represents the number 0, 1, 2 or 3,

R represents methyl, ethyl, n- or i-propyl, or n- or i-butyl, and

X represents nitro, cyano, halogen or represents optionally cyano-, halogen- or $C_1$–$C_4$-alkoxy-substituted alkyl, alkoxy, alkylthio, alkylsulphinyl or alkylsulphonyl having 1 to 4 carbon atoms, except for the compounds N-methyl-5-chlorodifluoromethyl-1,3,4-thiadiazol-2-yl-oxyacetanilide, N-ethyl-5-chlorodifluoromethyl-1,3,4-thiadiazol-2-yl-oxyacetanilide, 4-chloro-N-methyl-(5-chlorodifluoromethyl-1,3,4-thiadiazol-2-

TABLE B

Post-emergence test/greenhouse

| Active compound of Preparation Example No. | Application rate (g of ai./ha) | Maize | Setaria | Galium | Xanthium |
|---|---|---|---|---|---|
| 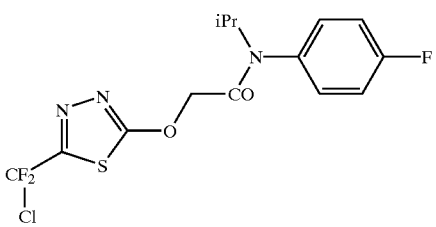 (1) | 1000 | 30 | 95 | 95 | 80 | yl)-oxyacetanilide and 3-trifluoromethyl-N-methyl-(5-chlorodifluoromethyl-1,3,4-thiadiazol-2-yl)-oxyacetanilide, N-i-propyl-5-chlorodifluoromethyl-1,3,4-thiadiazol-2-yl-oxyacetanilide, and 4-fluoro-N-methyl-(5-chlorodifluoromethyl-1,3,4-thiadiazol-2-yl)-oxyacetanilide and 4-fluoro-N-ethyl-(5-chlorodifluoromethyl-1,3,4-thiadiazol-2-yl)-oxyacetanilide.

2. The compound of claim 1, wherein n represents the number 0, 1 or 2,

R represents methyl, ethyl, n- or i-propyl, or n- or i-butyl, and

X represents nitro, cyano, fluorine, chlorine, bromine or represents optionally cyano-, fluorine-, chlorine-, methoxy- or eihoxy-substituted methyl, ethyl, n- or i-propyl, methoxy, ethoxy, methylthio, ethylthio, methylsulphinyl, ethylsulphinyl, methylsulphonyl or ethylsulphonyl.

3. The compound of claim 1, wherein n represents the number 0, 1 or 2,

R represents methyl, ethyl, or n- or i-propyl, and

X represents nitro, cyano, fluorine, chlorine, bromine or represents optionally fluorine- or chlorine-substituted methyl, ethyl, methoxy, ethoxy, methylthio, ethylthio, methylsulphinyl, ethylsulphinyl, methylsulphonyl or ethylsulphonyl.

4. The compound of claim 1, wherein n represents the number 0, 1 or 2,

R represents methyl, ethyl, or n- or i-propyl, and

X represents cyano, fluorine, chlorine, bromine, methyl, ethyl, trifluoromethyl, methoxy or trifluoromethoxy.

5. A process for preparing a compound of claim 1 comprising:

reacting 5-chlorodifluoromethyl-2-methylsulphonyl-1,3,4-thiadiazole of the formula (II)

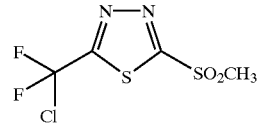

(II)

with a hydroxyacetanilide of the general formula (III)

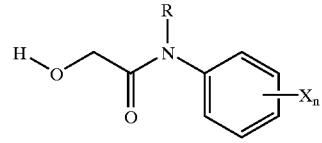

(III)

wherein n, R and X are as defined in claim 1; and collecting the reaction product.

6. A method for controlling plant growth comprising applying at least one compound of claim 1 to the plant and/or its habitat.

7. A herbicidal composition comprising a compound of claim 1 and at least one of extenders and surfactants.

8. The compound of claim 1, wherein n represents the number 0, 1 or 2,

R represents i-propyl, and

X represents cyano, fluorine, chlorine, bromine, methyl, ethyl, trifluoromethyl, methoxy or trifluoromethoxy.

* * * * *